United States Patent [19]

Mull

[11] 4,387,725
[45] Jun. 14, 1983

[54] DEVICE FOR USE IN THE COLLECTION AND TRANSPORTATION OF MEDICAL SPECIMENS

[76] Inventor: John D. Mull, 4088 Lakeshore Rd., E., Burlington, Ontario, Canada, L7L 1A1

[21] Appl. No.: 233,273

[22] Filed: Feb. 10, 1981

[51] Int. Cl.³ .................... A61B 10/00; A12K 1/00
[52] U.S. Cl. ............................. 128/759; 435/295
[58] Field of Search ............... 128/759; 206/209, 210, 206/222, 361; 435/295, 294

[56] References Cited

U.S. PATENT DOCUMENTS

| | | | |
|---|---|---|---|
| 3,776,220 | 12/1973 | Monaghan | 128/759 |
| 3,890,204 | 6/1975 | Avery | 128/759 |
| 3,913,564 | 10/1975 | Freshley | 128/759 |
| 3,923,604 | 12/1975 | Monaghan | 435/295 |
| 3,954,564 | 5/1976 | Mennen | 435/295 |
| 4,014,746 | 3/1977 | Greenspan | 128/759 |
| 4,014,748 | 3/1977 | Spinner et al. | 128/759 |
| 4,150,950 | 4/1979 | Fakeguchi et al. | 23/230 B |
| 4,223,093 | 9/1980 | Newman et al. | 435/295 |
| 4,312,950 | 1/1982 | Snyder et al. | 128/759 |

*Primary Examiner*—Kyle L. Howell
*Assistant Examiner*—Nancy A. B. Swisher

[57] ABSTRACT

A device for use in the collection and transportation of medical specimens is disclosed. The device includes a swab and a receptacle for the swab which contains a media material. The media material is retained in the receptacle by a septum which is penetrated when the swab is inserted after collection of a medical specimen so that the specimen is immersed in the media material. In one embodiment, the swab is initially housed in the receptacle at a first position and can be inserted further into the receptacle to penetrate the septum after a specimen has been collected. In another embodiment, the swab is initially separate from the receptacle.

4 Claims, 8 Drawing Figures

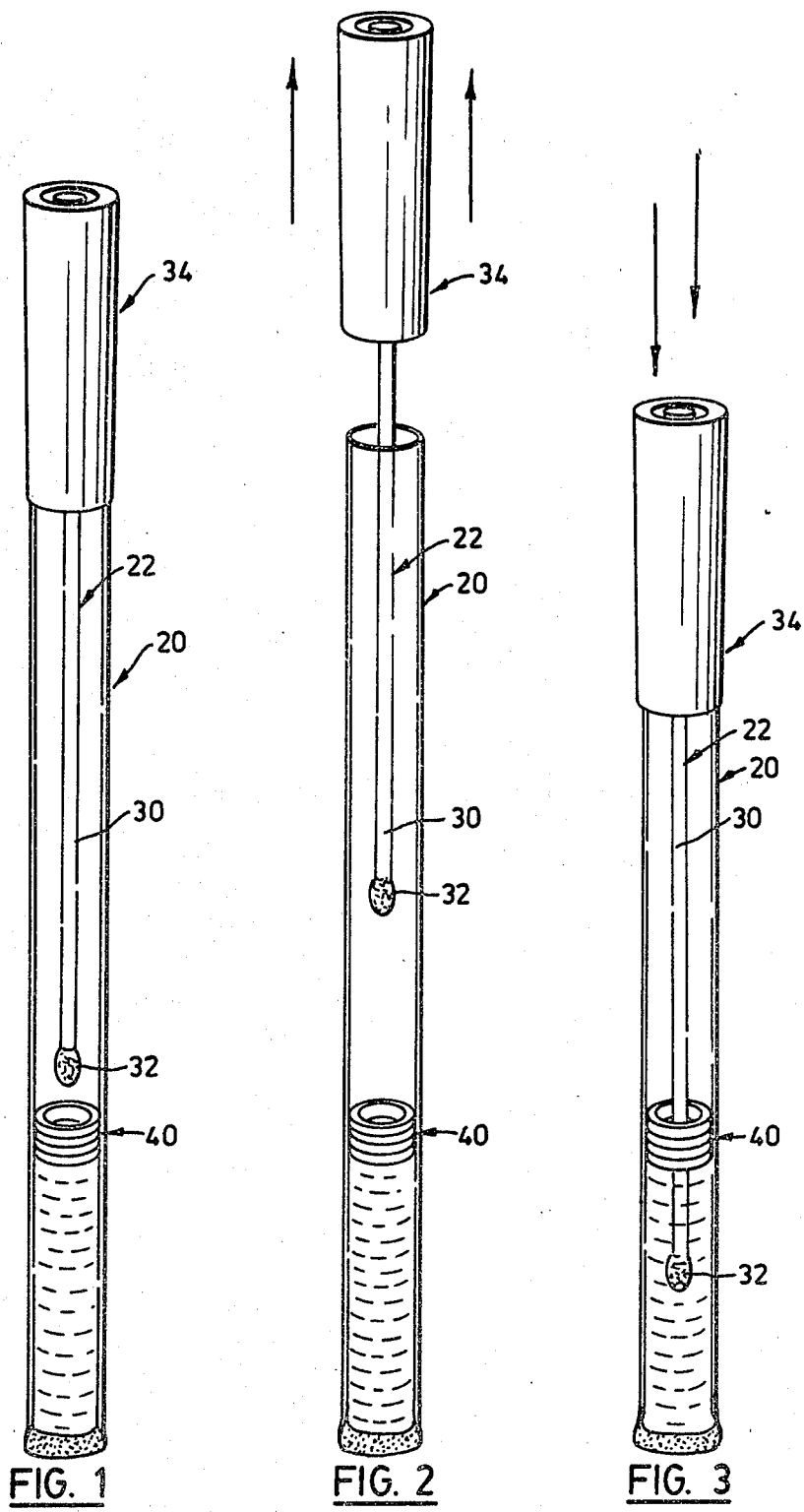

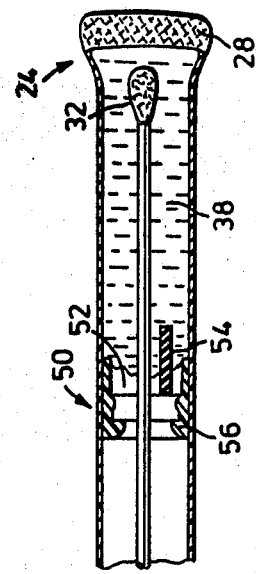
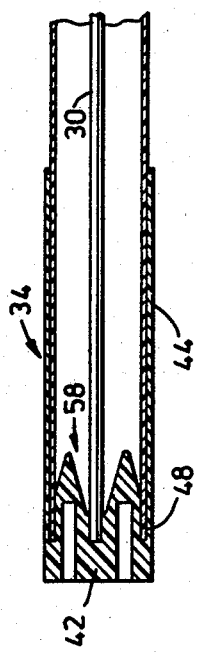
FIG. 5
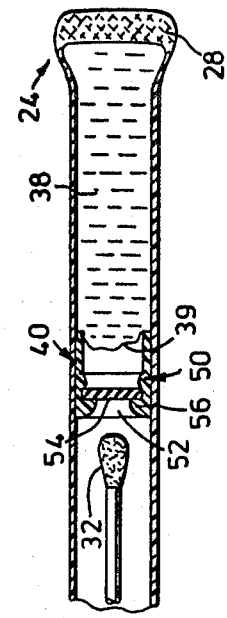
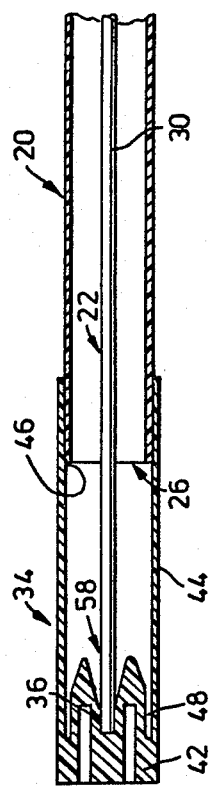
FIG. 4

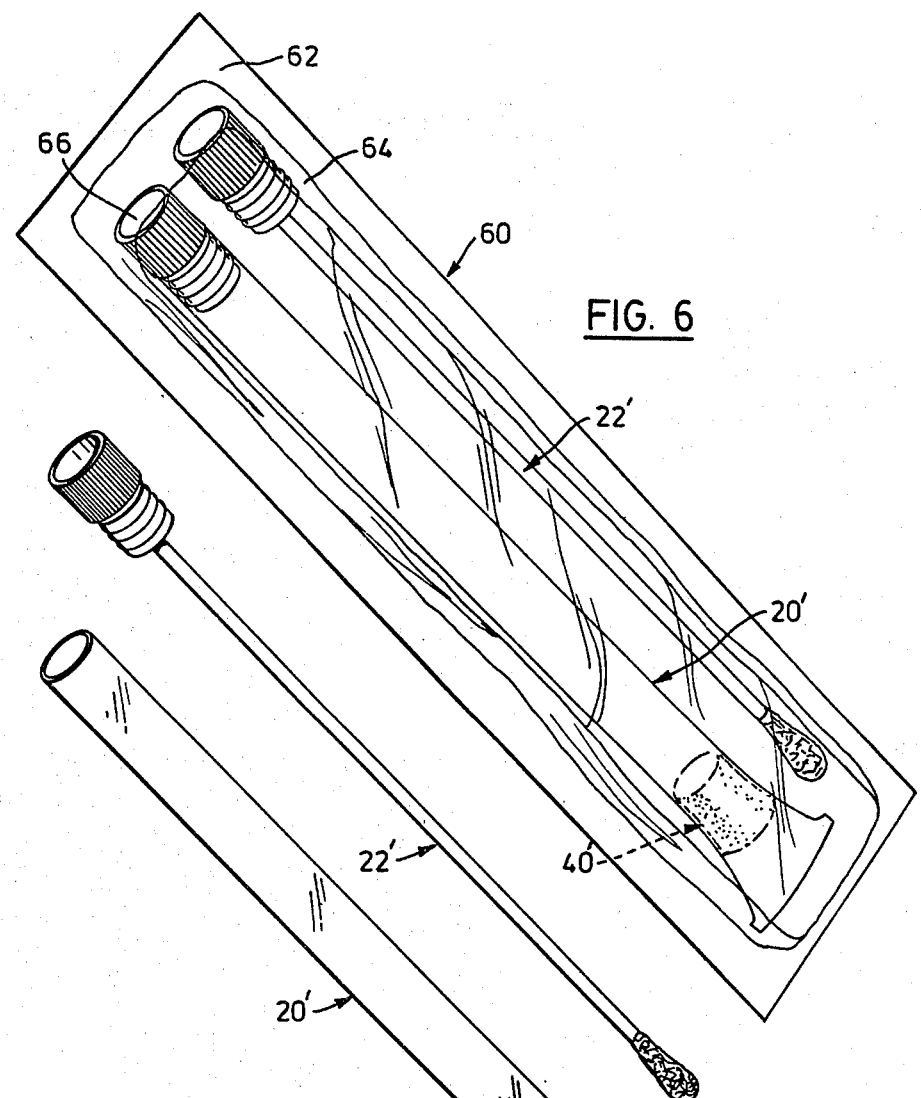
FIG. 6
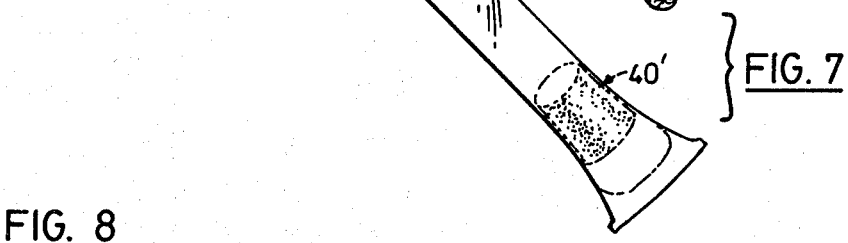
FIG. 7
FIG. 8
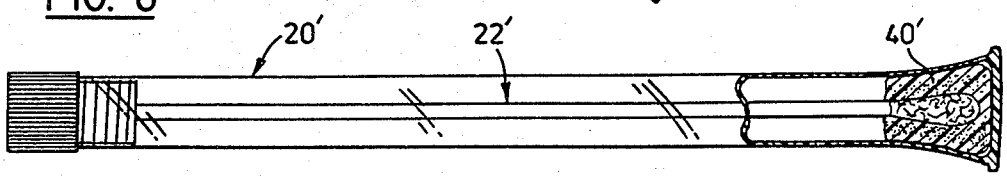

DEVICE FOR USE IN THE COLLECTION AND TRANSPORTATION OF MEDICAL SPECIMENS

This invention relates generally to devices for use in the collection and transportation of medical specimens.

In many medical procedures, it is necessary to collect a specimen from a patient using a swab and to transport the specimen to a laboratory for analysis. Ideally, the specimen should be preserved until it can be analyzed, in a condition as close as possible to its original condition. The specimen can then be used for what is termed "in vitro" diagnosis.

It has previously been proposed to provide a sterile receptacle into which the swab can be placed immediately after the specimen has been taken, and which contains a preservative liquid or jelly, for example Agar jelly. Typically, the preservative is a reducing agent and is often referred to as "media". The receptacle may be a flexible plastic tube into which a measured quantity of media has been introduced under sterile conditions and which is closed by a cap intended to be discarded when the receptacle is used. A sterile package comprising a receptacle of this form together with a swab has in fact been sold by the assignee of the present invention under the trade mark STARSWAB. In that case, the swab is fitted with a plug which seals the mouth of the receptacle when the swab is inserted; the swab then remains in the receptacle until it is opened for analysis.

While the STARSWAB (TM) sterile package has been found to be a vast improvement over prior specimen collection and transport methods, in some cases, the relatively small quantity of media typically provided in the receptacle may become dispersed inside the plastic tube (receptacle) if the tube is subjected to violent movement during transportation. In that case, the specimen does not remain immersed in media, and while this has not been found to detrimentally affect the specimen, the specimen is preserved under less than ideal conditions in those few cases in which this may happen. Breakdown of the dispersed media is also theoretically possible if the receptacle is subjected to extremes of temperature.

Other prior art devices have been proposed in which the media is contained within a glass vial in a flexible plastic receptacle. The invention is that, prior to inserting the swab into the receptacle, the plastic tube is pinched to break the vial and release the media. The obvious disadvantage of this type of device derives from the presence of glass fragments inside the receptacle, which might lead to the receptacle being punctured or, more likely, the possibility of injury to the technician who opens the receptacle.

An object of the present invention is to provide an improved device for use in the collection and transportation of medical specimens.

The device provided by the invention includes a receptacle in the form of an elongate transparent tube having a closed end and an open end and a swab comprising an elongate element having an absorbent pad at an outer end thereof and a cap at its opposite end. The cap is adapted to be fitted to the tube so as to close said open end and the element is arranged to extend outwardly from the cap into the tube when the cap is in place on the tube. A body of media material is disposed in the tube adjacent its closed end. A septum is positioned in the tube at a spacing from the closed end thereof selected so that the media material substantially fills the space between the septum and said closed end. The swab is dimensioned to cause its said outer end to penetrate the septum when the swab cap is in its said position closing the open end of the tube, whereby said absorbent pad enters the body of media material.

In one aspect of the invention the cap of the swab has a top wall to which the elongate element is fitted, and a cylindrical sheath which extends outwardly from the top wall around the element. The sheath is dimensioned to fit closely around the tube adjacent its open end in a first position in which the cap closes the open end of the tube while the swab remains clear of the septum, and the sheath is adapted to be moved to a second position in which the swab penetrates the septum while the cap maintains its closure of said open end of the tube.

According to the above-described aspect of the invention, the swab will be disposed within the receptacle at all times other than when a specimen is being taken. In other words, in the device as sold, the swab will be within the receptacle and the cap will be fitted to the receptacle so that the sheath is in said first position in which the absorbent pad is maintained clear of the septum. After the specimen has been taken, the swab will be refitted to the tube but this time with the sheath in the second position so that the septum will be penetrated by the absorbent pad of the swab.

According to an alternative aspect of the invention, the swab may be initially separate from the receptacle and the receptacle may be provided with a cap which initially closes the receptacle and which is intended to be discarded immediately after the specimen has been taken and before the swab is inserted into the receptacle. In this case, the receptacle (with cap) and swab will normally be sold together in a sterile package. In either aspect of the invention, the septum may take the form of a sponge for maintaining the media material in the space between the septum and the closed end of the receptacle tube. In this case, the media material will normally be at least partly absorbed into the sponge and the septum will be considered to have been penetrated when the absorbent pad of the swab enters the sponge; the swab will not normally project through the sponge.

In order that the invention may be more clearly understood, reference will now be made to the accompanying drawings which illustrate a number of preferred embodiments of the invention by way of example, and in which:

FIG. 1 is a perspective view of a device for use in the collection and transportation of medical specimens according to a first embodiment of the invention;

FIGS. 2 and 3 are sequential views similar to FIG. 1; FIG. 2 shows the swab being removed from the receptacle preparatory to taking a specimen, while FIG. 3 shows the swab having been returned to the receptacle and moved to a position at which the septum has been penetrated by the swab;

FIGS. 4 and 5 are longitudinal sectional views corresponding to FIGS. 1 and 3 respectively;

FIG. 6 is a perspective view of a sterile package comprising a swab and receptacle according to a further embodiment of the invention;

FIG. 7 shows the swab and receptacle and of FIG. 6 separate from the packaging material immediately prior to insertion of the swab into the receptacle; and, FIG. 8 is a perspective view, partly in section, showing the swab inserted into the receptacle and having penetrated the septum.

Reference will first be made to FIGS. 1 and 4, both of which show the device ready for use; that is, immediately before a medical specimen has to be taken. Normally, the device will be sold in a sterile package such as that shown in FIG. 6. The package will carry instructions for using the device and will have a space on which the patient from whom the particular specimen is taken can be identified. The device is intended for one time use only and will normally be discarded along with the packaging after the specimen has been analyzed.

Referring now particularly to FIGS. 1 and 4, the device comprises a receptacle 20 and a swab 22. The receptacle is in the form of an elongate and relatively flexible plastic tube having a closed end 24 and an open end 26 (FIG. 4). Reference numeral 28 denotes a heat seal formed during manufacture of the tube to close the relevant end. Swab 22 comprises an elongate element denoted 30, which in this case takes the form of a hollow plastic straw, having an absorbent pad 32 at an outer end thereof, and a cap 34 at its opposite end. The pad 32 is formed by a section of cotton batten secured by adhesive to the straw. At its opposite end, the straw is tightly push fitted into a recess 36 in the cap. The cap and straw should be fitted together with relative security so that the swab as a whole can be manipulated and used to take a specimen by a person holding the cap. The cap itself will be described in some detail later. For present purposes it is sufficient to note that the cap is designed to be fitted to the tube so as to close its open end with the element extending outwardly from the cap and into the tube as shown.

A body 38 of media material is disposed in the tube adjacent its closed end. In this particular embodiment, the media material is Agar jelly and has the consistency of a semi-solid; the outer surface of the material is shown as an uneven line denoted 39 in FIG. 4. A septum generally denoted 40 is positioned in the tube at a spacing from its closed end 24 selected so that the media material substantially fills the space between the septum and the closed end of the tube. As indicated above, the swab is dimensioned so that its outer end will penetrate the septum when the cap is fitted to the tube after a specimen has been taken so that the absorbent pad 32 will enter the media material.

In the embodiment shown in FIGS. 1 to 5, the cap of the swab is designed to be fitted to the tube 20 in either of two positions, in the first of which the absorbent pad 32 of the swab is maintained clear of the septum as best shown in FIG. 4, while in the second position, the swab penetrates the septum and enters the media material as best shown in FIG. 5. Thus, cap 34 comprises a top wall 42, to which the straw is fitted, and a sheath 44 which extends outwardly from the top wall around the straw. The sheath is dimensioned to be slidably fitted closely around the tube in the vicinity of its open end 26. Thus, the cap closes the open end of the tube at all times. The cap is shown in FIG. in its first position in which the absorbent pad 32 is clear of the septum. Thus, the inner wall of the sheath is recessed very slightly to define a ridge 46 against which the top edge of the tube seats when the swab is in its first position. The ridge is very narrow but is sufficient to provide a perceptable "seat" for defining the first position of the swab. As indicated above, the device as sold will normally be in this form and will appear from the outside as shown in FIG. 1. When a specimen is to be taken, the sheath will be grasped and pulled outwardly as shown in FIG. 2, removing the swab from the receptacle so that the specimen can be taken. When the specimen has been taken, the swab is inserted back into the receptacle as shown in FIG. 3 and the sheath is fitted over the open end of the tube and returned to the position shown in FIG. 1. When the sheath reaches the seat defined by ridge 46, it is pressed sharply inwardly with respect to the tube so that the upper end of the tube passes over the ridge and the outer end of the swab penetrates the septum as shown in FIG. 5. The sheath is then moved further in until it reaches the fully seated position shown in FIG. 5 in which the upper end of the tube 20 seats in an annular recess 48 (FIG. 5) inside the sheath. In this position, the absorbent pad 32, with the specimen thereon, is completely immersed within the media material 36 and the device can be transported to a laboratory for analysis of the specimen. The media material will tend to remain in the lower portion of the tube due to its semisolid nature; in any event, the parts of the septum which remain will assist in retaining the media material.

In this embodiment, the septum 40 comprises a sleeve 50 which is a friction fit inside tube 20 and which has an internal passageway 52 through which the swab can pass. The passageway is normally closed by a disc-shaped diaphragm 54 which is press-fitted into an annular recess inside sleeve 50. The diaphragm is shown in this position in FIG. 4 and is designed so that it will snap out of the recess when the swab is pressed against the diaphragm. It will be noted that an annular lip 56 (FIG. 5) is provided at the side of the diaphragm remote from the media material so that the diaphragm cannot accidentally be dislodged by the material. In this particular embodiment, the sleeve 50 is moulded in a polypropylene plastic material and the daiphragm is made of butyl rubber. The tube 20 can be automatically filled with media material on a tube filling machine and the septum can be readily pushed into the tube before it has been filled.

Referring back to cap 34, it will be noted from FIG. 5 that an integral stopper formation 58 projects from the top wall of the cap and is designed to fit inside the open end of the tube 20 so as to ensure positive sealing of the tube. The recess 36 which receives straw 30 is formed centrally of this formation.

Reference will now be made to FIGS. 6, 7 and 8 in describing an alternative embodiment of the invention. Primed reference numerals will be used in those views to denote parts which correspond with parts shown in FIGS. 1 to 5.

FIG. 6 shows a sterile package generally denoted 60 comprising a backing sheet 62 and a "blister" type transparent plastic cover 64 which encloses a receptacle 20' and a swab 22'. In this embodiment, the receptacle and swab are initially separate and the receptacle is provided with a stopper 66 which simply fits into the open end of the tube and which is discarded immediately before the swab is inserted into the tube. The tube itself is otherwise the same as the tube 20 described in connection with the preceeding embodiment and is fitted with a septum 40'. However, in contrast to the preceeding embodiment, the septum in this case takes the form of a cylindrical section of sponge closely fitted inside the tube. The sponge retains the filter media 36' in the lower end portion of the tube and will at least partly absorb media material.

Swab 22' is essentially very similar to the swab 22 described previously except in that cap has been replaced by a stopper which is essentially the same as the tube stopper 66.

When a specimen is to be taken, the package 60 is opened and the swab and receptacle are removed and the swab is used to take the specimen. The stopper 66 is then removed from the receptacle and discarded and the receptacle and swab would then be as shown in FIG. 7. The swab is then inserted into the receptacle and the stopper fitted into the mouth of the receptacle tube. As the swab is progressively inserted into the tube, the absorbent pad at the outer end of the swab will penetrate the septum 40' represented by the sponge in this case and will push the sponge to the lower end of the tube, coming to rest as shown in FIG. 8 with the pad disposed within the sponge. By this time, the sponge will be fully saturated with media material so that the specimen on the absorbent pad will be totally immersed in that material. The swab/receptacle combination is then returned to the package and the package is marked to identify the patient and then transported to the laboratory for analysis.

It will of course be appreciated that the preceeding description relates to specific embodiments of the invention and that many modifications are possible within the broad scope of the claims. For example, the particular constructional features and materials referred to are not essential. Media material other than Agar jelly may of course be used. For example, in some cases, it may be desirable to employ a solution especially prepared to preserve particular micro-organisms during transportation to a laboratory.

I claim:

1. A device for use in the collection and transportation of medical specimens comprising:
   a receptacle in the form of an elongate transparent tube having a closed and an open end;
   a swab comprising an elongate element having an absorbent pad at an outer end thereof, and a cap at its opposite end, the cap being adapted to be fitted to said tube so as to close said open end and the element being arranged to extend outwardly from the cap into the tube when the cap is in place on the tube;
   a body of media material disposed in said tube adjacent the closed end thereof; and,
   a penetrable septum positioned in the tube at a spacing from said closed end selected so that said media material substantially fills the space between the septum and said closed end, the swab being dimensioned so that its said outer end will penetrate the septum when the cap is in its said position closing the open end of the tube, whereby the absorbent pad with the specimen thereon will become immersed in the media material;
   said septum comprising a sleeve retained inside said tube and defining an internal passageway and a diaphragm normally closing said passageway, said passageway being dimensioned to permit the swab to pass therethrough when the cap is moved to said position closing the open end of the tube, and said diaphragm being received in an internal annular recess in side sleeve defined at the side of the diaphragm remote from the media material by an annular lip adapted to prevent dislodgement of the diaphragm in a direction away from the media material, and at the opposite side of the diaphragm by portions of the sleeve adapted to permit the diaphragm to be displaced from said recess by said swab in penetrating the septum.

2. A device as claimed in claim 1, wherein said cap comprises a top wall to which said elongate element is fitted and a cylindrical sheath which extends outwardly from said top wall around said element, said sheath being dimensioned to fit closely around said tube adjacent its open end in a first position in which the cap closes the open end of the tube while the swab is clear of said septum, said sheath defining a seat against which said end of the tube is located in said first position but over which the tube can ride as a result of further inward displacement of the cap towards a second position of said sheath in which the swab penetrates the septum while maintaining said closure of the open end of the tube.

3. A device as claimed in claim 2, wherein said cap is formed internally with a plug portion which depends from said top wall and which is adapted to fit inside and seal the open end of said tube when the cap is in its said second position.

4. A sterile package comprising a device as claimed in claim 1 enclosed in a transparent plastic blister formed at a side of a backing card.

* * * * *